US005743733A

United States Patent [19]
Crosland

[11] Patent Number: 5,743,733
[45] Date of Patent: Apr. 28, 1998

[54] MECHANICAL DENTAL ARTICULATOR HAVING ADJUSTABLE CLAMING FEATURE AND METHOD OF USE

[76] Inventor: Larry Crosland, 142 Roberts Ave., New York, N.Y. 13207-1348

[21] Appl. No.: 601,526

[22] Filed: Feb. 14, 1996

[51] Int. Cl.$^6$ ............................................. A61C 11/00
[52] U.S. Cl. ............................................. 433/57; 433/63
[58] Field of Search ............................. 433/57, 59, 63, 433/65

[56] References Cited

U.S. PATENT DOCUMENTS

| | | | |
|---|---|---|---|
| Re. 23,498 | 5/1952 | Stoll | 32/32 |
| 198,853 | 1/1878 | Oehlacker . | |
| D. 204,381 | 4/1966 | Orofino | D24/1 |
| 501,741 | 7/1893 | Simpson | 433/65 |
| 1,517,922 | 12/1924 | Stanley | 433/57 |
| 1,654,453 | 12/1927 | Brown | 433/65 X |
| 2,237,050 | 4/1941 | Franwick | 32/32 |
| 2,262,574 | 11/1941 | Chott | 32/32 |
| 2,621,407 | 12/1952 | Schlesinger | 433/65 X |
| 2,644,233 | 7/1953 | Shmukler et al. | 433/63 |
| 3,409,986 | 11/1968 | Freeman | 433/58 |
| 3,414,977 | 12/1968 | Cayo | 433/57 |
| 3,769,708 | 11/1973 | Guichet | 32/32 |
| 4,164,074 | 8/1979 | Lawler et al. | 433/65 |
| 4,412,822 | 11/1983 | Blechner | 433/57 X |
| 4,417,873 | 11/1983 | Kulas | 433/57 |
| 4,509,919 | 4/1985 | Gerbellot-Barrillon | 433/57 |
| 5,006,065 | 4/1991 | Waysenson | 433/54 |
| 5,007,829 | 4/1991 | Farrell | 433/57 X |
| 5,015,182 | 5/1991 | Newberry | 433/60 |

*Primary Examiner*—Nicholas D. Lucchesi
*Attorney, Agent, or Firm*—Trapani & Molldrem

[57] ABSTRACT

A dental articulator is claimed which comprises an upper frame, a lower frame, a positioning member for positioning the upper frame, and a clamp for securing the positioning member and fixing the upper frame in position. The upper frame includes a hinge such that a mounting portion of the frame can be moved through basic opening and closing mandibular movements. The mounting portions of the upper and lower frames are configured to accept for fixation upper and lower dental models respectively. The positioning member is coupled at one end to the upper frame for pivotal movement, such that an inclination of the upper frame relative to the lower frame can be effected. The positioning member is configured and dimensioned to position the upper frame in opposing relationship with the lower frame such that an articulation of upper and lower dental models can be effected. The other end of the positioning member is free to allow manual adjustment of the upper frame relative to the lower frame, to effect a proper functional occlusion of the dental models. The clamp for the positioning member is disposed adjacent to the lower frame.

14 Claims, 4 Drawing Sheets

MECHANICAL DENTAL ARTICULATOR HAVING ADJUSTABLE CLAMING FEATURE AND METHOD OF USE

BACKGROUND OF THE INVENTION

1. Technical Field

The present invention relates to dental articulators, and more particularly to dental articulators that have a wide range of adjustments to facilitate the construction of dental prostheses with proper occlusion.

2. Background Art

Dental articulators have been used by dentists and other dental providers for over one-hundred years to construct dental prostheses such as dentures. Over the years, three general classes of articulators have evolved - "nonadjustable," semi-adjustable, and "fully adjustable" articulators. Non-adjustable articulators, such as the hinge or fixed-guide types, are intended for making very simple fixed and removable prostheses, such as crowns and some partial dentures. Semi-adjustable articulators are intended for making all forms of removable prostheses and for moderately complicated fixed prosthodontic replacements. Fully adjustable articulators are intended for treating patients whose jaw movement patterns are not normal and for making complete fixed prosthodontic restorations.

Semi-adjustable and fully adjustable articulators possess a number of adjustments and controls which, while making these devices more versatile than the non-adjustable types, have, heretofore, increased the cost and the complexity of operating these devices as compared to non-adjustable types. As a result, in practice, most dentists and dental laboratories use non-adjustable articulators to make most of the fixed and removable dental prostheses, including full dentures and fixed prosthodontic replacements. Examples of these more basic articulators, having little or no adjustment, are disclosed in U.S. Pat. No. 1,517,922 to Stanley; U.S. Pat. No. 2,262,574 to Chott; and U.S. Pat. No. Des. 204,381 to Orofino.

Although simple to use and inexpensive, these non-adjustable (or limited adjustment) articulators have obvious drawbacks. Such articulators do not have the capability for correction or adjustment of a patient's oral bite registration without undergoing the lengthy and costly processes of re-articulation (i.e., re-adjustment and re-mounting the patient's dental models or casts on the articulator). These articulators are very limited in the number of mandibular positions they can assume. Most are restricted to the open and closed positions, while some permit limited lateral or protrusive excursions. This limitation on positioning and movement imposes a severe constraint on the dental provider in constructing even moderately complicated prostheses. In those non-adjustable articulators that offer some positioning and movement, there is usually no provision for fixing or locking the device in a desired position. Adjustment of position, or movement, usually requires the use of both hands, thus making it impossible for the dental provider to work on the mounted dental models or prostheses.

As a result of the above-noted drawbacks to the "nonadjustable" type of articulators, dental providers find themselves making adjustments by performing re-articulations, re-constructing prostheses, and/or grinding prostheses for proper functional occlusion. These activities increase the time and materials spent per case, which results in a higher cost per case. This cost is ultimately born by the patient. The patient is also inconvenienced by additional dental office visits.

The semi-adjustable and fully adjustable articulators evolved out of the need for a more versatile device that could avoid the above-noted drawbacks. However, due, in part, to the design goal to provide anatomically accurate mandibular movements and highly refined adjustments, these devices became very complex to operate and expensive. Extensive training was required to properly operate and obtain the benefits offered by these devices. As a result, these devices have not received widespread use among dentists and by dental laboratories. In fact, many schools of dentistry do not train their students on fully adjustable articulators due to the practical realization that dentists are not likely to use such devices in practice.

Attempts have been made to provide a full range of adjustments in an articulator in order to replicate accurate mandibular movements. For example, U.S. Pat. No. 5,006,065 to Waysenson, U.S. Pat. No. 4,417,873 to Kulas, and U.S. Pat. No. 3,409,986 to Freeman, all disclose such attempts. However, none of these articulators have fulfilled the longstanding need for a simple, easy-to-use, and inexpensive articulator for making all forms of dental prostheses. In addition, these articulators have not adequately addressed the need to minimize or eliminate the likelihood of having to perform a re-articulation step.

U.S. Pat. No. 5,015,182 to Newberry was an attempt to reduce the difficulties associated with re-articulation by providing clamps to removably secure the dental models. However, the Newberry articulator fails to offer a range of adjustments that can obviate the need for re-articulation. U.S. Pat. No. 5,006,065 to Waysenson and U.S. Pat. No. 198,853 (1878) to Oehlecker offer a full range of adjustments in the X,Y and Z axes. However, these articulators require substantial supporting and positioning apparatus to effect the X,Y and Z axes adjustments. Such intricate apparatus add to the cost of these articulators and makes them cumbersome to use.

OBJECTS AND SUMMARY OF THE INVENTION

It is therefore an object of the present invention to provide an adjustable dental articulator that overcomes the problems associated with the prior art.

It is another object of the present invention to provide an adjustable dental articulator that is simple in construction, easy to use, and inexpensive.

It is yet another object of the present invention to provide an adjustable dental articulator that permits re-adjustment of an incorrect oral bite registration without re-articulation.

It is still another object of the present invention to provide an adjustable dental articulator that can adjust dental models through a full range of mandibular positions.

It is a further object of the present invention to provide an adjustable dental articulator with a provision for locking or fixing a dental model in a selected mandibular position, so that the dental provider is free to work on the dental model.

It is yet a further object of the present invention to provide an adjustable dental articulator that is versatile enough to minimize the need to re-construct or grind prostheses for proper functional occlusion.

It is still a further object of the present invention to provide an adjustable dental articulator that is economical to manufacture.

It is still yet a further object of the present invention to provide an adjustable dental articulator which is suitable as a teaching aid at dental schools.

It is still yet a further object of the present invention to provide a method of correcting a patient's dental bite registration without re-articulation.

These and other objects are obtained in accordance with the present invention wherein there is provided a dental articulator, comprising an upper frame, a lower frame, a positioning member for positioning the upper frame, and a clamp for securing the positioning member and fixing the upper frame in a desired position relative to the lower frame.

In the preferred embodiment, the upper frame includes a mounting member and a coupling member. The mounting member is pivotally connected to the coupling member such that the mounting member can be moved through basic opening and closing mandibular movements. The mounting member is configured and dimensioned to accept for fixation an upper dental model which replicates a patient's maxilla. The lower frame includes a mounting member and a base member. The mounting member is configured and dimensioned to accept for fixation a lower dental model which replicates the patient's mandible.

In the preferred embodiment, the positioning member is a single, elongated post having a coupling end and a free end. The coupling member of the upper frame is configured to couple to the coupling end of the positioning member for pivotal movement. The positioning member is configured and dimensioned to position the upper frame in opposing relationship with the lower frame such that an articulation of upper and lower dental models can be effected. The free end of the positioning member facilitates manual adjustment of the position of the upper frame relative to the lower frame to effect proper functional occlusion of the upper and lower dental models. Lateral, protrusive and vertical positioning of the upper frame can be performed by directly manipulating the positioning member and upper frame. The upper frame (attached to the positioning member) is free to move along a direct path to a desired operating position.

In the preferred embodiment, the clamp for the positioning member is disposed adjacent to the base member of the lower frame. The clamp is configured to secure the positioning member and fix the position of the upper frame. The position of the clamp is adjustable in order to accommodate a full range of positions to be assumed by the positioning member. The clamp should be simple in construction and easy to adjust. Preferably, the clamp is configured like a simple hand-operated vise, with a pair of clamping plates in opposed spaced relationship. Like a vise, the position of the pair of spaced clamping plates is adjustable such that the positioning member can be clamped at different lateral positions.

In the preferred embodiment, the coupling of the positioning member to the coupling member of the upper frame permits pivotal movement of the upper frame about the X, Y and Z axes (identified in FIG. 1). Movement about the X axis permits inclined (or pitch) positioning of the upper frame relative to the lower frame. A locking or clamping cap is preferably included at the coupling point of the positioning member and upper frame, for securing the upper frame in a fixed orientation relative to the positioning member (and lower frame during operation).

BRIEF DESCRIPTION OF THE DRAWING

Further objects of the present invention will become apparent from the following description of the preferred embodiments with reference to the accompanying drawing, in which.

DESCRIPTION OF THE PREFERRED EMBODIMENTS

Figure 1:
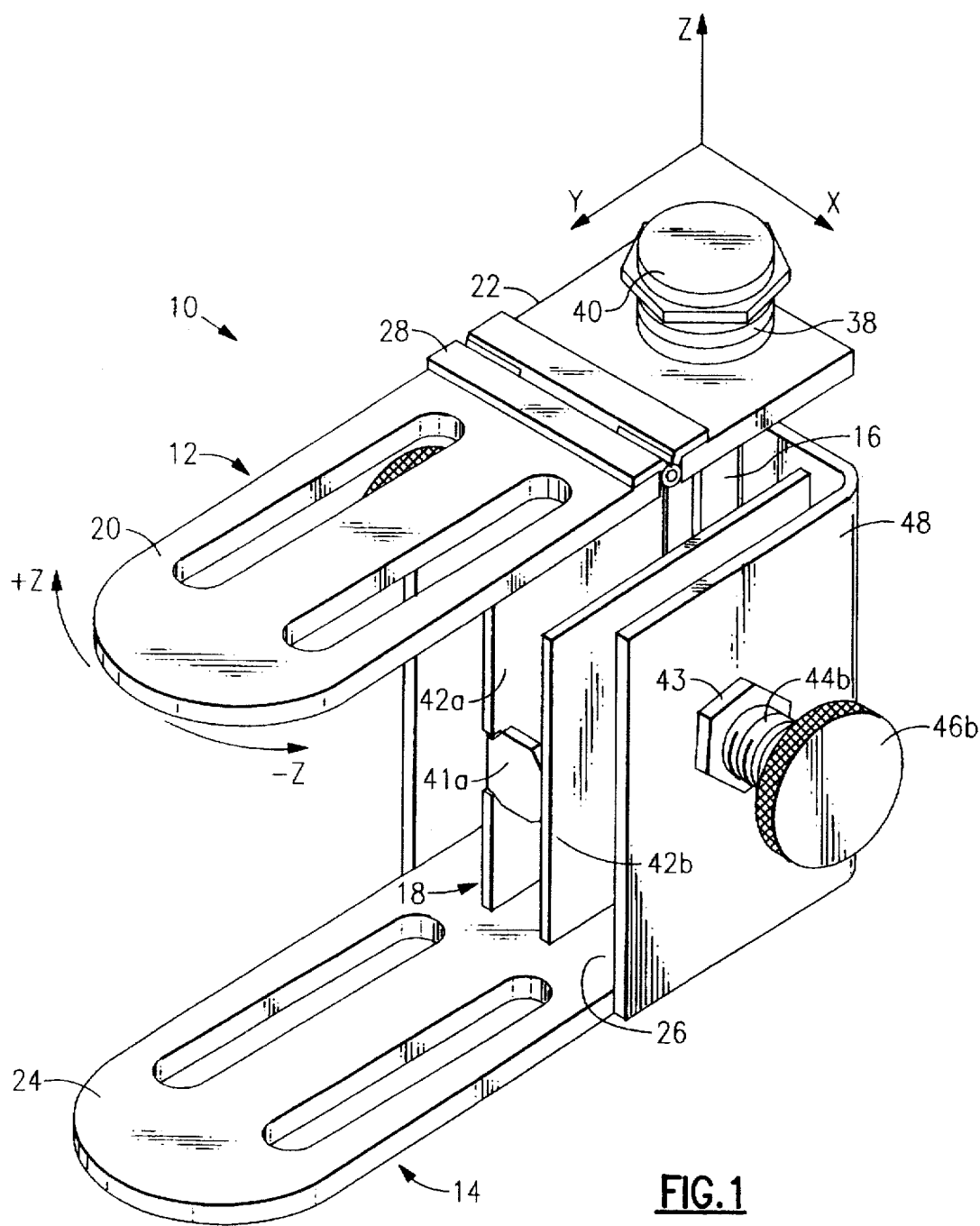
FIG. 1 is a perspective view of the adjustable dental articulator of the present invention.

With reference to FIG. 1, there is shown a perspective view of an adjustable dental articulator 10 constructed in accordance with the present invention. Articulator 10 comprises an upper frame 12, a lower frame 14, a positioning member 16, and a clamp 18. Upper frame 12 includes a mounting member 20 and a coupling member 22. Lower frame 14 includes a mounting member 24 and a base member 26.

Figure 2:
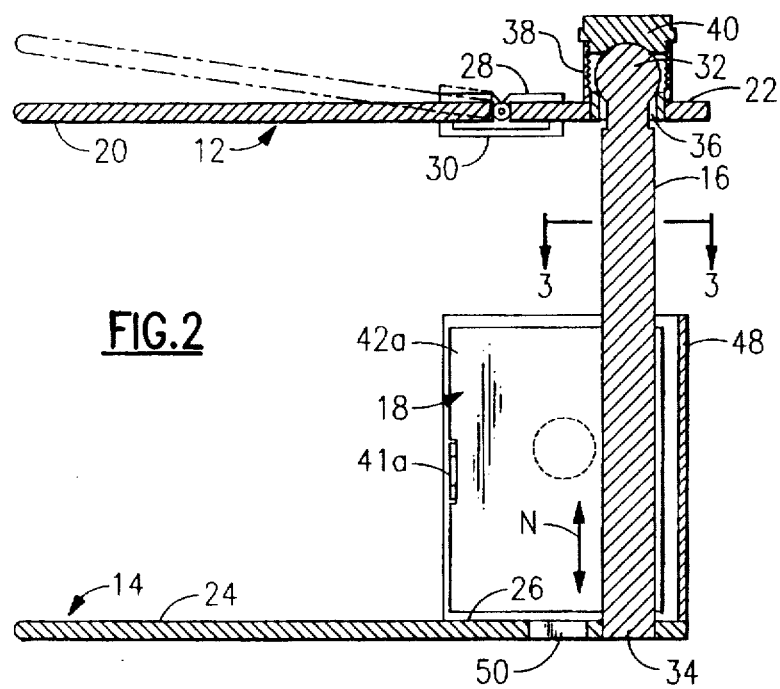
FIG. 2 is a cross sectional view of the adjustable dental articulator of FIG. 1, showing the mounting member of the upper frame in a normal rest position and in a slightly elevated position (in phantom lines)

As shown in FIGS. 1 and 2, mounting member 20 is connected to coupling member 22, preferably, by a simple hinge 28. This hinged connection permits mounting member 20 to be manually elevated upward from an initial rest position (shown in FIG. 1) and lowered to the initial rest position, to simulate the basic human mandibular movements of opening and closing. This simulated mandibular movement is illustrated, in part, in FIG. 2, by showing an elevated mounting member 20 in phantom lines. Mounting member 20 is stopped at the rest position by a stop arm 30, as shown in FIG. 2. Stop arm 30 is welded to the underside of coupling member 22 at its proximal end, and is unattached at its distal or stopping end.

As shown in FIG. 1, mounting members 20 and 24 are configured and dimensioned in a conventional manner to accept upper and lower dental models (or casts) respectively (not shown). As is well known in the dental art, such models are affixed to the mounting members using a bonding compound, clay, plaster of paris, or the like. As is well understood in the art, the dental models are casts produced from oral bite impressions taken directly from the patient's maxilla and mandible.

As shown in FIG. 2, positioning member 16 is a single, elongated post having a coupling end 32 and a free end 34. Positioning member 16 preferably has a square or rectangular cross-section as shown in FIGS. 3–6. As shown in FIG. 2, coupling member 22 contains a hole 36 which has a diameter large enough to allow positioning member 16 to pass therethrough, except for coupling end 32. Coupling end 32 is substantially spherical in shape, with a diameter greater than the diameter of hole 36. Coupling member 22 further includes an internally threaded flange 38 to which a threaded locking or clamping cap 40 can be threaded. Cap 40 functions like a clamp. If cap 40 is loosely threaded into flange 38, it allows frame 12 to pivotally move about coupling end 32. If cap 40 is tightly threaded into flange 38, cap 40 bears down on coupling end 32, causing upper frame 12 to be fixed in orientation relative to positioning member 16.

Figure 8:
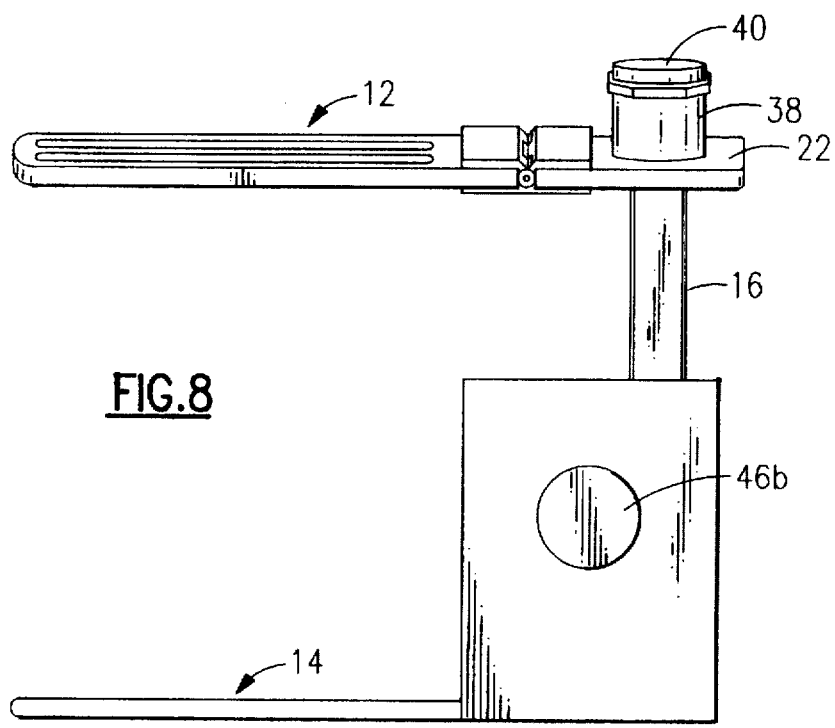
FIG. 8 is a side elevation view of the dental articulator of the present invention, showing the upper frame rotated slightly about the Y axis.
Figure 9:
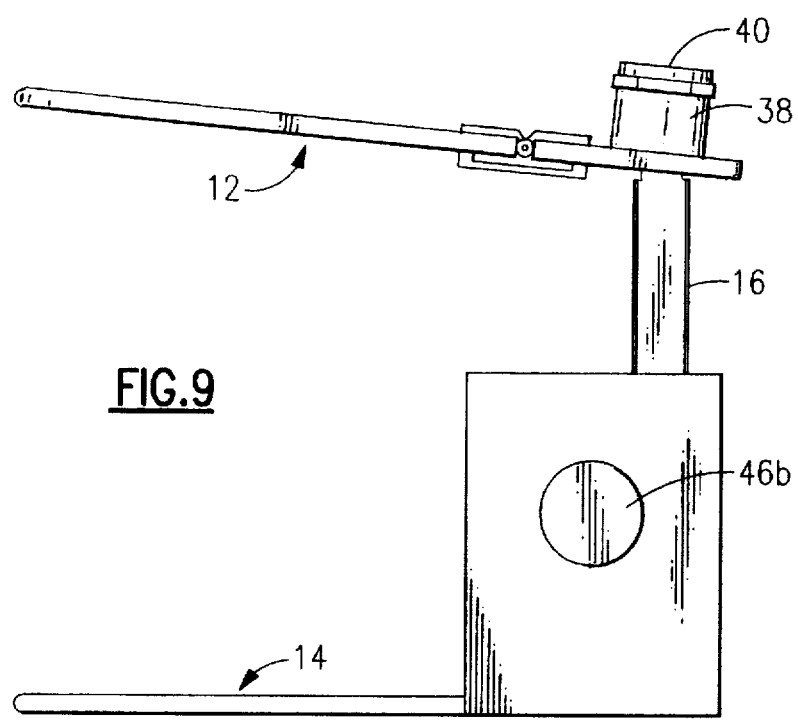
FIG. 9 is a side elevation view of the dental articulator of the present invention, showing the upper frame elevated slightly about the X axis.
Figure 10:
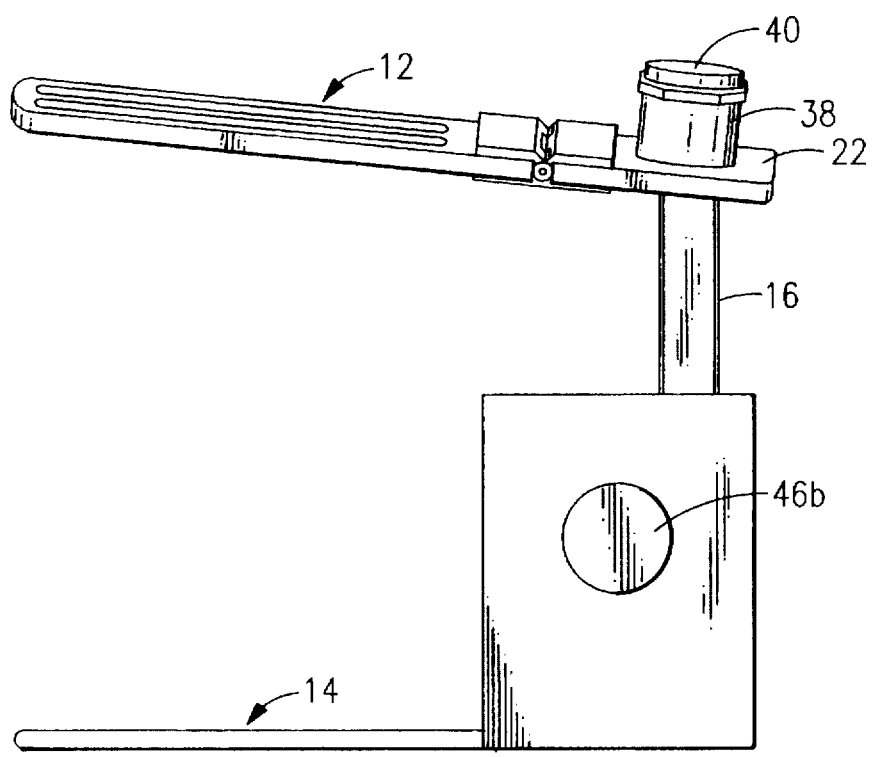
FIG. 10 is a side elevation view of the dental articulator of the present invention, showing the upper frame rotated slightly about the Y axis and elevated slightly about the X axis.

As understood from FIGS. 1 and 2, the arrangement of end 32 coupled to member 22 provides for pivotal movement of upper frame 12 about the three-dimensional axes, X, Y, and Z (shown in FIG. 1). Movement of upper frame 12 about the X axis permits positive and negative (relative to horizontal) inclined positioning of the upper frame relative to the lower frame. FIG. 9 illustrates positive inclined positioning of upper frame 12 about the X axis. Similarly, frame 12 may be moved to a negative inclined position, i.e., downward from horizontal. FIG. 8 illustrates pivotal movement (i.e., rolling) and positioning of upper frame 12 about the Y axis, in a clockwise direction (if looking in the —Y direction). Similarly, frame 12 can be moved (or rolled) and positioned about the Y axis in the counterclockwise direction. Arrows +z and −z, in FIG. 1, represent the pivotal movement and positioning of upper frame 12 about the Z axis. FIG. 10 illustrates the versatility of the pivotal coupling by showing frame 12 rotated slightly about the Y axis and elevated slightly about the X axis.

As shown in FIGS. 1 and 2, positioning member 16 positions upper frame 12 in opposing relationship with lower frame 14, such that an articulation of upper and lower dental models can be effected. Positioning member 16 is typically dimensioned to have a length of $3^{13}/_{16}$ inches, which provides a sufficient vertical displacement between upper frame 12 and lower frame 14 (when in operation). The vertical displacement between frame 12 and frame 14 is selected to allow for articulation of statistically average upper and lower dental models (which are to be mounted on the frames). If greater vertical displacement is necessary, positioning member 16 merely has to be elevated from base 26 and secured by clamp 18. Articulator 10 may also include a number of positioning members of different lengths (e.g., average length, smaller than average length, and larger than average length), to be used alternately, to accommodate the full spectrum of dental model sizes experienced in practice.

Free end 34 of positioning member 16 facilitates manual adjustment of the position of upper frame 12 relative to lower frame 14. This "free-end" adjustment of upper frame 12 makes it easy to effect a proper articulation of the upper and lower dental models, affixed to mounting members 20 and 24 respectively. Lateral, protrusive and vertical positioning of upper frame 12 can be performed by directly manipulating positioning member 16 and upper frame 12. Upper frame 12 (attached to positioning member 16) is free to move along a direct path, selected by the operator to reach a desired operating position. The feature that positioning member 16 is "floating" (i.e., unattached to a base or some positioning apparatus), permits unimpeded exercise of hand-eye coordination during the process of manually positioning upper frame 12 relative to lower frame 14. This feature makes the articulator, of the present invention, easy to use.

Clamp 18 is configured to secure positioning member 16, and thereby fix the general position of upper frame 12 relative to lower frame 14. The position of clamp 18 is adjustable in order to accommodate a full range of positions assumed by positioning member 16. Clamp 18 should be simple in construction and easy to adjust by hand.

Figures 3, 4:
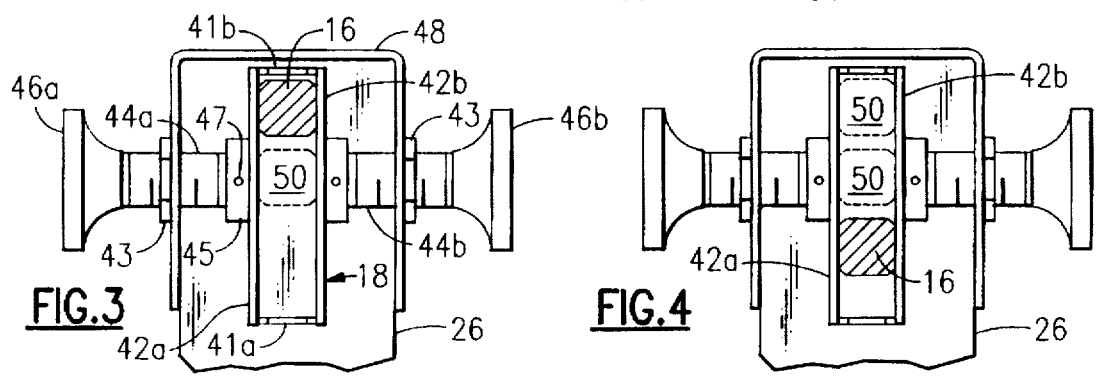
FIGS. 3–6 is a series of top views taken along line 3—3 in FIG. 2, illustrating four different positions of the positioning member and clamp relative to the base member of the lower frame.

As shown in FIGS. 1 and 3, clamp 18 is configured like a simple hand-operated vise. It includes a pair of spaced clamping plates 42a and 42b, in opposed relationship, and disposed substantially normal to the X axis. Plate 42a includes a spacer tab 41a, and plate 42b includes a spacer tab 41b. The function of spacer tabs 41a and 42b is to stabilize plates 42a and 42b (i.e., maintain them in a parallel relationship), while plates 42a and 42b are clamping positioning member 16.

Plate 42a is rotatably coupled to a threaded adjusting screw 44a which includes a thumb wheel head 46a. Similarly, plate 42b is rotatably coupled to a threaded adjusting screw 44b which includes a thumb wheel head 46b. Adjusting screws 44a and 44b are supported by an upright collar 48, at opposing side walls respectively. As shown in FIG. 3, collar 48 contains a bore through each opposing side wall, which is dimensioned to receive screws 44a and 44b. Welded to each opposing side wall of collar 48, and aligned with its respective bore, is a threaded nut 43. Screws 44a and 44b are threaded through their respective nut 43.

The rotatable coupling of adjusting screws 44a and 44b to plates 42a and 42b, respectively, is accomplished by a slip collar 45 welded to each plate, as shown in FIG. 3. The ends of screws 44a and 44b extend into collars 45 and are dimensioned such that they can rotate inside collars 45. A circumferential groove (not shown) is contained near the end of each screw 44a and 44b. Each screw end is retained inside its respective collar 45 by a pair of set screws 47 (only one of which is shown for each collar in FIGS. 3–6). Set screws 47 slidably engage the circumferential groove contained in the screw end to effect the rotatable coupling.

Figures 5, 6:
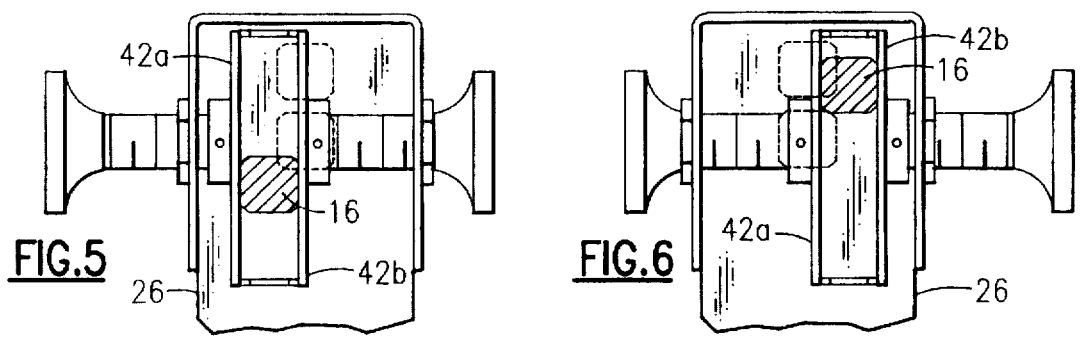

The positions of clamping plates 42a and 42b are adjustable (substantially along the X axis) by rotating thumb wheel heads 46a and 46b respectively. Positioning member 16 is secured in a fixed position by rotating either or both of thumb wheel heads 46a and 46 clockwise until clamping plates 42a and 42b are urged against the shank of positioning member 16 (See FIGS. 3–6). As illustrated in FIGS. 5–6, lateral positioning of positioning member 16 is achieved by adjustment of the positions of clamping plates 42a and 42b.

As shown in FIGS. 2–7, base member 26 may optionally contain one or two station holes 50. Holes 50 provide typical operating locations for positioning member 16; but, by no means is the operation of the dental articulator of the present invention limited to these locations. In fact, hole or holes 50 are not necessary for the operation of articulator 10. Hole or holes 50 also provide a location for storing positioning member 16 when articulator 10 is not in use.

With further reference to FIGS. 3–6, there is shown a series of top views, taken along line 3—3 in FIG. 2, illustrating four different positions of positioning member 16 and clamp 18. In FIG. 3, positioning member 16 is situated in the rear-most hole 50, and secured in place by clamp 18. This position of member 16 is also shown in the sectional view of FIG. 2. FIG. 4 shows positioning member 16 clamped in a protrusive position, forward of holes 50. FIGS. 5 and 6 show positioning member 16 positioned in two extreme lateral positions. It is understood from FIGS. 3–6 that positioning member 16 may be positioned at a multiplicity of locations on the surface of base member 26, within the clamping reach of clamp 18. Further, it is understood from the drawing figures that positioning member 16 may be elevated from the surface of base member 26, and secured in an elevated position. Elevated positioning of positioning member 16 is represented by arrow N in FIG. 2. Positioning member 16 may also be lowered below the surface of base member 26 and clamped in position if one of holes 50 is utilized.

Figure 7:
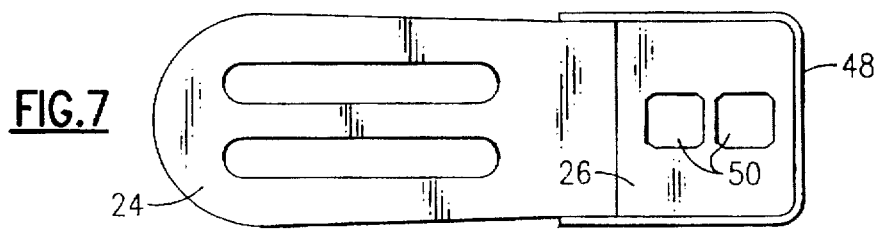
FIG. 7 is a top plan view of the adjustable dental articulator of the present invention, shown without the positioning member and upper frame.

Referring now to FIG. 7, there is shown a top plan view of articulator 10, without positioning member 16 and upper frame 12. This view clearly shows the arrangement of mounting member 24, based member 26, collar 48, and station holes 50.

In operation, articulator 10 is prepared for mounting the upper and lower dental models of a patient to upper and lower mounting members 20 and 24 respectively, as with any conventional articulator. The models are then mounted to upper and lower mounting members 20 and 24. Upper frame 12, coupled to positioning member 16, is fixed into an initial position by clamp 18. The orientation of upper frame 12, relative to positioning member 16, is adjusted to an initial setting, and fixed in position by tightening clamping cap Based on patient data, the position of upper frame 12 is adjusted laterally, protrusively, or vertically to effect proper bite registration (or functional occlusion). This latter positioning step is achieved by freeing positioning member 16 from clamp 18, adjusting the position of clamp 18 (if necessary), locating positioning member 16 in the desired adjusted position, and securing positioning member 16 in the desired adjusted position by tightening clamp 18.

Upper and lower dental models are articulated to confirm whether or not proper bite registration (i.e., functional occlusion) has been achieved. Articulation is performed by raising and lowering upper mounting member 20 on hinge 28 (See FIG. 2). Proper functional occlusion should occur at the rest position of mounting member 20 (i.e., when member 20 is stopped by stop arm 30).

If proper occlusion or bite registration is not achieved, this may indicate that: (1) one or both of the patient's dental models were incorrectly mounted to articulator 10; or (2) there was an error in making one or both of the patient's dental models. In the first case, improper bite registration may be readily corrected, without re-articulation, by loosening cap 40 and adjusting the orientation of upper frame 12 about the X, Y and/or Z axes. In the second case, a correction may be made in many cases depending upon the error made in the dental model (s). For, example, if oral bite registration is incorrect due to it being open in the back, this opening might be corrected (upon consultation with the treating dentist) by adjusting the orientation of upper frame 12, as in the first case.

The method of correcting a patient's dental bite registration without re-articulation can be summarized by the following steps. First, the patient's upper and lower dental models are mounted to upper and lower frames 12 and 14 respectively. Second, the upper dental model is positioned in opposing relationship with the lower dental model to effect an articulation of the models. In the preferred embodiment, this is accomplished using dental articulator 10 of the present invention, as hereinabove described. Third, the bite registration of the upper dental model with the lower dental model is examined. Fourth, if found to be incorrect, the dental bite registration is corrected by adjusting the position of upper frame 12 relative to lower frame 14, in one or more of the X, Y and Z axes.

Articulator 10 may be constructed of the same materials used to construct conventional articulators. Preferably, the material is any suitable metal, such as bronze or chrome.

While the preferred embodiments of the invention have been particularly described in the specification and illustrated in the drawing, it should be understood that the invention is not so limited. Many modifications, equivalents, and adaptations of the invention will become apparent to those skilled in the art without departing from the spirit and scope of the invention as defined in the appended claims.

What is claimed is:

1. A dental articulator, comprising:
  a first frame, configured to accept for fixation thereto a first dental model;
  a second frame, configured to accept for fixation thereto a second dental model;
  a positioning member having one end attached to said first frame and another end, said positioning member being configured and dimensioned to position said first frame in opposing relationship with said second frame, the other end of said positioning member facilitating manual adjustment of said first frame relative to said second frame; and
  clamping means for receiving the other end of said positioning member and allowing adjustment of said other end along a least two axes, said clamping means being adapted to secure said other end in an adjusted position.

2. A dental articulator as recited in claim 1, wherein said positioning member is pivotally attached to said first frame such that an inclination of said first frame relative to said second frame can be effected.

3. A dental articulator as recited in claim 1, wherein the other end of said positioning member facilitates lateral, protrusive and occlusive positioning of said first frame relative to said second frame.

4. A dental articulator as recited in claim 1, wherein said first frame includes a mounting member and an attachment member, the mounting member being pivotally connected to said attachment member such that the mounting member can be moved through basic opening and closing mandibular movements, said mounting member being configured and dimensioned to accept a dental model for fixation thereto, said positioning member being pivotally attached to said attachment member of said first frame.

5. A dental articulator as recited in claim 4, wherein said second frame includes a mounting member and a base member, the mounting member being configured and dimensioned to accept the second dental model for fixation thereto.

6. A dental articulator as recited in claim 4, wherein the pivotal attachment of said positioning member to the attachment member of said first frame permits movement of said first frame about the X axis when said first frame is in opposing relationship with said second frame.

7. A dental articulator as recited in claim 6, wherein the pivotal attachment of said positioning member to the attachment member of said first frame permits movement of said first frame about the X and Y axes when said first frame is in opposing relationship with said second frame.

8. A dental articulator as recited in claim 7, wherein the pivotal attachment of said positioning member to the attachment member of said first frame permits movement of said first frame about the X, Y and Z axes when said first frame is in opposing relationship with said second frame.

9. A dental articulator as recited in claim 8, wherein the pivotal attachment of said positioning member to the attachment member of said first frame includes locking means for securing said first frame in a fixed orientation relative to said positioning member.

10. A dental articulator as recited in claim 9, wherein said clamping means is disposed adjacent to the base member of said lower second frame, and includes a pair of spaced clamping plates in opposing relationship and disposed substantially normal to the X axis, the space between said clamping plates being adjustable for clamping said positioning member in a fixed position, the position of said pair of spaced clamping plates being adjustable along the X axis such that said positioning member can be clamped at different lateral positions.

11. A dental articulator as recited in claim 10, wherein said positioning member is a single, elongated post.

12. A dental articulator, comprising:
- an upper frame, including a mounting member and a coupling member, the mounting member being pivotally connected to said coupling member, said mounting member being configured and dimensioned to accept for fixation thereto an upper dental model;
- a lower frame, including a mounting member and a base member, the mounting member being configured and dimensioned to accept for fixation thereto a lower dental model;
- an elongated positioning member having a coupling end and a free end, the coupling member of said upper frame being configured to couple to the coupling end of said positioning member for pivotal movement, such that an inclination of said upper frame relative to said lower frame can be effected,
- said positioning member being configured and dimensioned to position said upper frame in opposing relationship with said lower frame, the free end of said positioning member facilitating manual adjustment of said upper frame relative to said lower frame; and
- clamping means, being disposed adjacent to the base member of said lower frame, for receiving the free end of said positioning member and allowing adjustment of the free end along at least two axes, said clamping means being adapted to secure the free end in an adjusted position.

13. A dental articulator as recited in claim 12, wherein the free end of said positioning member facilitates lateral, protrusive and occlusive positioning of said upper frame relative to said lower frame.

14. A method of correcting dental bite registration without re-articulation using an articulator which includes, first and second frames, a positioning member having one end attached to the first frame and another end, and a clamp in which the other end of the positioning member is received and allowed to be adjusted along at least two axes, said method comprising the steps of:
- (a) mounting an upper dental model to the first frame of said articulator;
- (b) mounting a lower dental model to the second frame of said articulator;
- (c) positioning the upper dental model in opposing relationship with the lower dental model to effect an articulation of said models;
- (d) examining the bite registration of the upper dental model with the lower dental model; and
- (e) correcting the bite registration by
  - (i) adjusting the position of the other end of the positioning member along at least two axes in the clamp, and
  - (ii) securing said other end in the adjusted position with the clamp.

* * * * *

UNITED STATES PATENT AND TRADEMARK OFFICE
CERTIFICATE OF CORRECTION

PATENT NO. : 5,743,733
DATED : April 28, 1998
INVENTOR(S) : Larry Crosland

It is certified that error appears in the above-identified patent and that said Letters Patent is hereby corrected as shown below:

In col. 7, line 15, "cap" should read --cap 40.--

Col. 8, lines 16-20 should read:
--clamping means, into which said positioning member extends, for allowing adjustment of the other end of said positioning member along at least two axes and for securing said positioning member in an adjusted position--.

In col. 8, line 64, "lower second frame" should read --second frame--.

Col. 10, lines 10-12 should read:
-- attached to the first frame and another end, and a clamp into which the positioning member extends, said --.

In col. 10, lines 27-28, "in the clamp" is deleted.

Col. 10, lines 29-30 should read:
--(ii) securing said positioning member in an adjusted position with the clamp--.

Signed and Sealed this

Twenty-ninth Day of September, 1998

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,743,733

DATED : April 28, 1998

INVENTOR(S) : Larry Crosland

It is certified that error appears in the above-identified patent and that said Letters Patent is hereby corrected as shown below:

The title should read:

--MECHANICAL DENTAL ARTICULATOR HAVING ADJUSTABLE CLAMPING FEATURE AND METHOD OF USE--.

Signed and Sealed this

Twenty-seventh Day of April, 1999

*Attest:*

Q. TODD DICKINSON

*Attesting Officer*  Acting Commissioner of Patents and Trademarks